United States Patent [19]

Dumican et al.

[11] Patent Number: 4,633,873

[45] Date of Patent: Jan. 6, 1987

[54] SURGICAL REPAIR MESH

[75] Inventors: Barry L. Dumican, Newtown; Alan L. Kaganov, Stamford; Thomas A. Ritter, Bristol, all of Conn.

[73] Assignee: American Cyanamid Company, Stamford, Conn.

[21] Appl. No.: 604,104

[22] Filed: Apr. 26, 1984

[51] Int. Cl.⁴ .................. A61F 13/00; A61L 15/04; A61B 17/00
[52] U.S. Cl. ............................................. 128/334 R
[58] Field of Search ............... 128/334 R, 1 R, 335.5

[56] References Cited

U.S. PATENT DOCUMENTS

| | | | |
|---|---|---|---|
| 3,124,136 | 3/1964 | Usher | 128/334 |
| 3,463,158 | 8/1969 | Schmitt et al. | 128/334 |
| 3,736,646 | 6/1973 | Schmitt et al. | 128/335.5 |
| 3,797,499 | 3/1974 | Schneider | 128/334 R |
| 3,875,937 | 4/1975 | Schmitt et al. | 128/156 |
| 4,520,821 | 6/1985 | Schmidt et al. | 128/334 R |

OTHER PUBLICATIONS

"Splenic Capping: An Experimental Study . . . Using Woven Polyglycolic Acid Mesh", H. M. Delany, et al., Ann. Surg. 196 187–193 (1982).

Primary Examiner—Jacqueline V. Howard
Attorney, Agent, or Firm—Charles F. Costello, Jr.

[57] ABSTRACT

A mesh or fabric, having zero to variable stretch, is made from absorbable or partially absorbable fibers. The mesh or fabric can be either knitted or woven. The fabric is useful in surgical repair.

10 Claims, No Drawings

SURGICAL REPAIR MESH

BACKGROUND AND SUMMARY OF THE INVENTION

This invention is concerned with a mesh or fabric which may be either knit or woven. The fabric is made from either a tissue absorbable material such as polyglycolic acid (herein PGA) fibers, or from a partially tissue absorbable material such as mixtures of PGA fibers and fibers of a nonabsorbable polyester or polyamide, or fibers of another medically acceptable nonabsorbable material. It is to be understood that the term polyglycolic acid is generic to both the homopolymer and to copolymers containing a glycolic acid ester linkage.

The mesh or fabric has varying amounts of stretch, including zero stretch in the warp or in the weft (filling) direction.

The mesh or fabric may be useful in a wide variety of internal surgical procedures, e.g. as a tamponading device for pressure encapsulation and repair of traumatically damaged organs such as the spleen, liver or kidney. The mesh or fabric may also be useful as a zero stretch or low stretch material e.g. in the repair of an abdominal wall defect, hernia, urinary tract, etc. Further, the mesh or fabric may be useful in areas of the cardiovascular system and in the brain. Still further, the mesh or fabric may be useful in oral surgery, for example to repair defects and to encourage tissue ingrowth.

Although the dimensions and weight of the mesh are only limited by the practical size for its intended use, dimensions of from 4×4 inches to 10×13 inches and weights of 0.75 to 6.5 ounces per square yard can be normally used. Openings in the mesh can range normally from zero to ¼ inch. The mesh can also be manufactured as a tubular prosthesis.

A drawing which describes the shape and/or geometrical configuration of the mesh or fabric is not necessary for an understanding of this invention. That is, any person skilled in the mesh or fabric art will know how to manufacture and how to use the invention by reading this specification, generally and the examples, specifically.

In order to further stabilize the fabric, that is to eliminate horizontal or vertical edge curling and regulate stretch, the fabric may be heat set by holding both length and width to a specified dimension within a pin or clip frame while exposing the material to temperatures of 90° to 175° C. for periods of 30 seconds to 15 minutes, preferably in a vacuum. The fabric may also be heat set by holding both the length and width to a specified dimension on a heated cylinder while exposing the material to temperatures of 90° to 175° C. for periods of up to 4 hours in a vacuum.

A knitted surgical mesh has been invented. The mesh comprises a plurality of filaments. Each filament is manufactured from a polymer having a glycolic acid ester linkage. The filaments are bundled or twisted into a yarn, and the yarn is knitted into a mesh.

In one embodiment, the polymer is a homopolymer. In another embodiment, the polymer is a copolymer. In a more specific embodiment, the copolymer is manufactured from glycolide and from trimethylene carbonate.

In yet another embodiment, the yarn manufactured from the homopolymer is greater than about 60 denier and contains up to 4 plys. Each ply has greater than about 25 filaments. In a more specific embodiment, the yarn is up to about 150 denier, and the total number of filaments per yarn is up to about 75.

In still another embodiment, the yarn manufactured from the glycolide and trimethylene carbonate copolymer is about 65 to 85 denier. The yarn contains about 5 to 25 filaments.

In still another embodiment, the knitted mesh is manufactured on a 14 gauge tricot knitting machine wherein the stitch design is

| Front Bar | (2/0 2/4) × 2 |
|---|---|
| | (4/6 4/2) × 2 |
| and Back Bar | (4/6 4/2) × 2 |
| | (2/0 2/4) × 2. |

In yet another embodiment, the weight of the mesh is about 4 to 10 oz./sq. yd. In a further embodiment, the quality of the mesh is about 10 to 20 inches per 480 courses.

A knitted surgical fabric has also been invented. The fabric comprises a plurality of filaments. Each filament is manufactured from a polymer having a glycolic acid ester linkage. The filaments are bundled or twisted into a yarn, and the yarn is knitted into a fabric.

In one embodiment, the polymer is a homopolymer. In another embodiment, the polymer is a copolymer. In a more specific embodiment, the copolymer is manufactured from glycolide and from trimethylene carbonate.

In yet another embodiment, the yarn manufactured from the polymer is up to about 150 denier and contains up to about 75 filaments. In a more specific embodiment, the yarn is about 100 to 135 denier and contains about 40 to 75 filaments.

In still another embodiment, the knitted fabric is manufactured on a 48 gauge Raschel knitting machine wherein the stitch design is

| Front Bar: | 1/0 0/1 |
|---|---|
| and Back Bar: | 1/0 4/5. |

In yet another embodiment, the weight of the fabtric is about 4 to 10 oz./sq. yd. In a further embodiment, the quality of the fabric is about 10 to 20 inches per 480 courses.

A woven surgical fabric has been invented. The woven fabric comprises a plurality of filaments. Each filament is manufactured from a polymer having a glycolic acid ester linkage. The filaments are twisted into a yarn, and the yarn is woven into a fabric.

In one embodiment, the polymer is a homopolymer. In another embodiment, the polymer is a copolymer. In a more specific embodiment, the copolymer is manufactured from glycolide and from trimethylene carbonate.

In yet another embodiment, the yarn manufactured from the polymer is less than about 300 denier, and the yarn contains at least about 3 plys. In a more specific embodiment, the yarn is about 40 to 250 denier and contains about 5 plys. The total number of filaments per yarn is about 50 to 150.

In a still further embodiment, the warp yarn of the woven fabric has about 2 to 7 twists per inch and the filling yarn has about ½ to 5 twists per inch. In a yet further embodiment, the weight of the fabric is about 1 to 6 oz./sq. yd.

DETAILED DESCRIPTION

The fabric of the invention can be either a knitted or a woven fabric. The fabric is of a medium weight.

One fabric of this invention, described more fully in Example 1 is a stretchable knit mesh. The mesh can be manufactured on a 14 gauge tricot machine, or alternatively on a 28 gauge Raschel warp knit machine using a 2-bar construction. On either of these machines, the mesh is not heat set.

The yarn used in knitting the mesh can be between about 150 to 600 denier with between 1 and 5 turns per inch of twist. Preferably, the mesh has a lock stitch construction for nonravelling.

The usefulness of this fabric is primarily in the area of organ repair. Specifically, this fabric may be most useful in soft organ repair, e.g., the spleen, liver or kidney. This fabric may also be useful in the repair of the pancreas. Finally, the utility of this fabric is as an organ sling during internal healing of the organ. However, this fabric can also be used as a retraction sling for other purposes, e.g. as a retraction sling for irradiation therapy.

Another fabric described in Examples 2 and 3 is a semistretchable knit mesh. It can be knit on a 28 gauge tricot machine using a 1-bar construction. The mesh can be knit from a yarn having about 30 to 100 denier.

The usefulness of this semistretchable knit mesh is in abdominal wall repair, hernia repair, or in oral surgery, as a temporary support or as a packing material for encouragement of tissue ingrowth.

Another fabric of this invention, which is described more fully in Examples 4 and 5, is also a knit fabric. The fabric is heat set without stretching, and is stabilized. The heat set can be on a tenter frame. The fabric can be manufactured on a 24 gauge tricot or 48 gauge Raschel machine using a 2-bar construction.

The fabric can be between about 75 to 250 denier with between about ¼ to 5 turns per inch. Preferably, the fabric is also manufactured using a chain stitch for stability.

The utility of this fabric can be in abdominal wall repair. Other uses can be for the repair of diaphragm defects. Still other uses can be as a rectal support for recurrent prolapse. Finally, the fabric may be useful for tracheal malacia.

Still another fabric of this invention, described in Examples 6 and 7, is a weave. The weave is stabilized. The fabric is manufactured on a loom.

The product is made from yarns of between about 150 to 350 denier. The warp yarn has between about 4 to 10 turns per inch of twist and the weft yarn has between about ¼ to 5 turns per inch of twist. The weave can be plain or it can have other configurations, e.g. twill or satin. Finally, the woven fabric has a water porosity of about zero to 1000 ml/min/cm$^2$ at 120 mm of mercury.

Examples of typical fabrics or mesh as contemplated by this invention are given below:

EXAMPLE 1

14 Gauge Tricot (14 needles/inch)

This example is a knitted mesh which has been neither stretched nor heat set.
(A) Stitch design:
Front bar: (2/0 2/4)×2, (4/6 4/2)×2
Back Bar: (4/6 4/2)×2, (2/0 2/4)×2
(B) Yarn description:
3 ply 110 den./50 fil. of polyglycolic acid (homopolymer)
(C) Fabric Weight:
5.0 to 7.5 oz./sq. yd.
(D) Fabric quality:
16 inches (per 480 courses)

EXAMPLE 2

28 Gauge Tricot (28 needles/inch)

This homopolymer example of a prior art glycolide and lactide copolymer tight knitted mesh has been both stretched and heat set. Further the knitted mesh has been prestressed, i.e., stretched prior to heat setting.
(A) Stitch Design:
Front bar: 1/0 1/2
Back bar: none
(B) Yarn description:
62 den./28 fil. of polyglycolic acid (homopolymer)
(C) Fabric weight:
1.00 to 2.75 oz./sq. yd.
(D) Fabric quality:
8 inches (per 480 courses)

EXAMPLE 3

28 Gauge Tricot (28 needles/inch)

This glycolide and trimethylene carbonate copolymer example of a prior art glycolide and lactide copolymer tight knitted mesh has been both stretched and heat set. The stitch design is the same as Example 2. Further, the knitted mesh has been prestressed, i.e., stretched prior to heat setting.
(A) Stitch design:
Front bar: 1/0 1/2
Back bar: none
(B) Yarn description:
75 den./12 fil. of a glycolide and trimethylene carbonate copolymer.
(C) Fabric weight:
1.00 to 2.75 oz./sq. yd.
(D) Fabric quality:
8 inches (per 480 courses)

EXAMPLE 4

48 Gauge Raschel or 24 Gauge Tricot (24 needles/inch)

This example describes a knitted fabric which has been heat set but not stretched.
(A) Stitch design:
Front bar: 1/0 0/1 (chain stitch)
Back bar: 1/0 4/5
(B) Yarn description:
123 den./56 fil. of polyglycolic acid (homopolymer)
(C) Fabric weight:
6.25±0.50 oz./sq. yd.
(D) Fabric quality:
14 inches (per 480 courses)

EXAMPLE 5

48 Gauge Raschel or 24 Gauge Tricot (24 needles/inch)

This example describes a knitted fabric which has been heat set but not stretched. The stitch design is the same as Example 4.
(A) Stitch design:
Front bar: 1/0 0/1 (chain stitch)
Back bar: 1/0 4/5
(B) Yarn description:

110 den./50 fil. of polyglycolic acid (homopolymer)
(C) Fabric weight:
  5.85±0.60 oz./sq. yd.
(D) Fabric quality:
  14 inches (per 480 courses)

EXAMPLE 6

1×1 Plain Woven Fabric

This example teaches a woven fabric which has been neither stretched nor heat set.
(A) Warp yarn and filling yarns: 5 ply 46 denier/21 fil. of polyglycolic acid (homopolymer)
(B) Warp yarn twist: 5 turns per inch
(C) Filling yarn twist: 1.5 turns per inch
(D) Fabric weight: 4.00±0.50 oz./sq. yd.

EXAMPLE 7

1×1 Plain Woven Fabric

This example teaches a woven fabric which has been neither stretched nor heat set.
(A) Warp yarn and filling yarns: 250 denier/50 fil. of a glycolide and trimethylene carbonate copolymer.
(B) Warp yarn twist: 5 twists per inch
(C) Filling yarn twist: 1.5 twists per inch
(D) Fabric weight: 4.00±0.50 oz./sq. yd.

We claim:

1. A stretchable, non-heat set knitted surgical mesh comprising a plurality of filaments, each filament manufactured from a polymer having a glycolic acid ester linkage, said filaments bundled to twisted into a yarn, and said yarn knitted into a mesh.

2. A knitted mesh of claim 1 wherein said polymer is a homopolymer.

3. A knitted mesh of claim 1 wherein said polymer is a copolymer.

4. A knitted mesh of claim 3 wherein said polymer is manufactured from glycolide and from trimethylene carbonate.

5. A knitted mesh of claim 2 wherein said yarn is greater than about 60 denier and contains up to 4 plys, each ply having greater than about 25 filaments.

6. A knitted mesh of claim 4 wherein said yarn is about 65 to 85 denier and contains about 5 to 25 filaments.

7. A knitted mesh of claim 5 wherein said yarn is up to about 150 denier, and the total numbers of filaments per yarn is up to about 75.

8. A knitted mesh of claim 5 or 7 manufactured on a 14 gauge tricot knitting machine wherein the stitch design is

| Front Bar | (2/0 2/4) × 2 |
| | (4/6 4/2) × 2 |
| and Back Bar | (4/6 4/2) × 2 |
| | (2/0 2/4) × 2. |

9. A knitted mesh of claim 8 wherein the weight of said mesh is about 4 to 10 oz./sq. yd.

10. A knitted mesh of claim 9 wherein the quality of said mesh is about 10 to 20 inches per 480 courses.

* * * * *